(12) United States Patent
Virolle et al.

(10) Patent No.: US 9,206,212 B2
(45) Date of Patent: Dec. 8, 2015

(54) ACTINOMYCETE STRAIN COMPOSITION AND ITS USE

(75) Inventors: Marie-Joëlle Virolle, Bures sur Yvette (FR); Hanane Hamdali, Beni Mellal (MA); Yedir Ouhdouch, Marrakech (MA); Mohamed Hafidi, Marrakech (MA); Ahmed Benharref, Marrakech (MA); Ahmed Lebrihi, Beni Mellal (MA); Marie Carmen Monje, Auzeville-Tolosane (FR)

(73) Assignees: CENTRE NATIONAL DE LA RECHERCHE SCIENTIFIQUE, Paris (FR); UNIVERSITE CADI AYYAD-FACULTE DES SCIENCES SEMLALIA, MARRAKECH-MAROC, Marrakech (MA)

(\*) Notice: Subject to any disclaimer, the term of this patent is extended or adjusted under 35 U.S.C. 154(b) by 0 days.

(21) Appl. No.: 14/233,194

(22) PCT Filed: Jul. 20, 2012

(86) PCT No.: PCT/EP2012/064357
§ 371 (c)(1),
(2), (4) Date: Apr. 8, 2014

(87) PCT Pub. No.: WO2013/011142
PCT Pub. Date: Jan. 24, 2013

(65) Prior Publication Data
US 2014/0221205 A1  Aug. 7, 2014

(30) Foreign Application Priority Data
Jul. 20, 2011 (EP) .................................... 11305948

(51) Int. Cl.
| | | |
|---|---|---|
| A01N 55/02 | (2006.01) |
| A01N 55/04 | (2006.01) |
| A01N 35/10 | (2006.01) |
| A01N 47/40 | (2006.01) |
| C07F 15/02 | (2006.01) |
| A01N 59/16 | (2006.01) |
| A01N 63/00 | (2006.01) |
| A01N 63/02 | (2006.01) |
| C12N 1/20 | (2006.01) |
| C12R 1/465 | (2006.01) |
| C12P 13/00 | (2006.01) |
| A61K 31/295 | (2006.01) |
| C07C 251/70 | (2006.01) |

(52) U.S. Cl.
CPC .............. *C07F 15/025* (2013.01); *A01N 35/10* (2013.01); *A01N 55/02* (2013.01); *A01N 59/16* (2013.01); *A01N 63/00* (2013.01); *A01N 63/02* (2013.01); *A61K 31/295* (2013.01); *C07C 251/70* (2013.01); *C12N 1/20* (2013.01); *C12P 13/001* (2013.01); *C12R 1/465* (2013.01)

(58) Field of Classification Search
None
See application file for complete search history.

(56) References Cited

U.S. PATENT DOCUMENTS 6,355,658 B1    3/2002  Reboud-Ravaux et al.
6,852,317 B2 *  2/2005  Lehman et al. ............... 424/115

FOREIGN PATENT DOCUMENTS

WO    2009/024528 A1    2/2009

OTHER PUBLICATIONS

ISR 1—International Search Report 1, dated Sep. 27, 2012, from corresponding PCT application.
ISR 2—International Search Report 2, dated Oct. 2, 2012, from corresponding PCT application.
H. Hamdali et al: "Physiological studies and comparative analysis of rock phosphate solubilization abilities of Actinomycetales originating from Moroccan phosphate mines and of *Streptomyces lividans*", Applied Soil Ecology, Elsevier, Amsterdam, NL, vol. 44, No. 1, Jan. 1, 2010, pp. 24-31.
H. Hamdali et al: "Theses doctorat: Criblage et caracterisation de souches de bacteries Actinomycetales solubilisatrices du phosphate naturel isolees a partir des gisements de phosphate marocains", Jan. 1, 2008, pp. 1-4.
H. Hamdali et al: "La solubilisation du phosphate mineral apatitique par les actinomycetes", Congres International: "Biotechnologie Microbienne Au Service Du Developpement", Marrakech, Maroc., Nov. 2, 2009, p. 85.
I. Kempen et al: "6-Substituted 2-oxo-2H-1-benzopyran-3-carboxylic acid derivatives in a new approach of the treatment of cancer cell invasion and metastasis", European Journal of Medicinal Chemistry, Editions Scientifique Elsevier, Paris, FR, vol. 43, No. 12, Dec. 1, 2008, pp. 2735-2750.
L. Pochet et al: "Esters and Amides of 6-(Chloromethyl)-2-oxo-2H-1-benzopyran-3-carboxylic Acid as Inhibitors of alpha-Chymotrypsin: Significance of the "Aromatic" Nature of the Novel Ester-Type Coumarin for Strong Inhibitory Activity", Journal of Medicinal Chemistry, American Chemical Society, US, vol. 39, Jan. 1, 1996, pp. 2579-2585.
C. Doucet et al: "6-substituted 2-oxo-2H-1-benzopyran-3-carboxylic acid as a core structure for specific inhibitors of human leukocyte elastase", Journal of Medicinal Chemistry, vol. 42, No. 20, Oct. 7, 1999, pp. 4161-4171.
S. Robert et al: "Novel 3-carboxamide-coumarins as potent and selective FXIIa inhibitors", Journal of Medicinal Chemistry, vol. 51, No. 11, Jun. 2008, pp. 3077 3080.
L. Pochet et al: "Coumarinic derivatives as mechanism-based inhibitors of alpha-chymotrypsin and human leukocyte elastase", Bioorganic & Medicinal Chemistry, Pergamon, GB, vol. 8, No. 6, Jun. 1, 2000, pp. 1489-1501.
R. Frederick et al: "3,6-Disubstituted Coumarins as Mechanism-Based Inhibitors of Thrombin and Factor Xa", Journal of Medicinal Chemistry, vol. 48, No. 24, Dec. 1, 2005, pp. 7592-7603.
P. Ovaere et al: "The emerging roles of serine protease cascades in the epidermis", Trends in Biochemical Sciences, Elsevier, Haywards, GB, vol. 34, No. 9, Sep. 1, 2009, pp. 453-463.

(Continued)

*Primary Examiner* — Alton Pryor
(74) *Attorney, Agent, or Firm* — Young & Thompson (57) ABSTRACT

Novel actinomycete strain composition and its use.

17 Claims, 4 Drawing Sheets

(56) References Cited

OTHER PUBLICATIONS

M. Paliouras et al: "The kallikrein world: an update on the human tissue kallikreins", Biological Chemistry, vol. 387, No. 6, Jun. 2006, pp. 643-652.

N. Komatsu et al: "Correlation between SPINK5 gene mutations and clinical manifestations in Netherton syndrome patients", Journal of Investigative Dermatology, vol. 128, No. 5, May 2008, pp. 1148-1159.

P. Fortugno et al: "Proteolytic Activation Cascade of the Netherton Syndrome-Defective Protein, LEKTI, in the Epidermis: Implications for Skin Homeostasis", The Society of Investigative Dermatology, vol. 131, No. 11, Jun. 23, 2011, pp. 2223-2232.

D. Secci et al: "Synthesis and selective human monoamine oxidase inhibition of 3-carbonyl, 3-acyl, and 3-carboxyhydrazido coumarin derivatives", European Journal of Medicinal Chemistry Editions Scientifique Elsevier, Paris, FR, vol. 46, No. 10, Jul. 9, 2011, pp. 4846-4852.

\* cited by examiner

ACTINOMYCETE STRAIN COMPOSITION AND ITS USE

The present invention relates to new actinomycete strain composition and its use.

Microorganisms have been the only living organism on the planet during several billions years. They are the most abundant and diversified living form on the earth. They represent a current total biomass of $10^{30}$ bacteria, assuming essential functions for life such as oxygen, carbon, nitrogen cycle being thus essential for the human being survival.

Many soil microorganisms able to solubilize mineral phosphates have been considered important for increasing phosphate (P) availability to the plants they associate with, allowing a sustainable use of chemical phosphate fertilizers (Gyaneshwar P, Kumar G N, Parekh L J, Poole P S. Role of soil microorganisms in improving P nutrition of plants. Pl Soil 245: 83-93 (2002)). The natural rock phosphate (RP), used in traditional agriculture, might indeed constitute a valuable alternative source of P fertilizer (Zapata F, Zaharah A R. Phosphorus availability from phosphate rock and sewage sludge as influenced by the addition of water-soluble phosphate fertilizer. Nut Cyc Agroecosys 63: 43-48 (2002)). The commercially available RP is composed of sparingly soluble apatite minerals (i.e., calcium hydroxyapatite $[Ca_{10}(PO_4)_6 OH]$ with some constitutive ions such as Fe, Al, Na, Mg), from which the phosphate (P) is generally unavailable for plant uptake (Takeda M, Knight J D. Enhanced solubilization of rock phosphate by *Penicillium bilaiae* in pH-buffered solution culture. Can J Microbiol 52: 1121-1129 (2006)) Several scientific reports mention that many phosphate solubilizing microorganisms (PSMs) dissolve insoluble mineral phosphates by three ways: (i) by the acidification of the environment through secretion of organic acids (Rodriguez H, Fraga R. Phosphate solubilizing bacteria and their role in plant growth promotion. Biotechnol Adv 17: 319-339 (1999)), (ii) by the production of chelating substances (Abd-Alla M H, Omar S A. Survival of *rhizobia*/badyrhizobia and rock-phosphate-solubilizing fungus *Aspergillus niger* on various carriers from some agro-industrial wastes and their effects on nodulation and growth of faba bean and soybean. J Plant Nutr 24: 261-272 (2001); Zhao X, Lin Q, Li B. The solubilization of four insoluble phosphates by some microorganisms. Wei Sheg Wu Xue Bao 42: 236-241 (2002)), by the competition of exchange reactions between phosphates and organic acids anions (Trolove S N, Hedley M J, Kirk G J D, Bolan N S, Loganathan P. Progress in selected areas of rhizosphere research on P acquisition. Aust J Soil Res 41: 471-499 (2003)). Among various PSMs studied, those secreting chelating substances have been poorly-characterized. Chelation involves the formation of two or more coordinated bonds between an anionic or a polar molecule and a cation, resulting in a ring structure complex (Whitelaw M A. Growth promotion of plants inoculated with phosphate-solubilizing fungi. Advances in Agronomy 69: 99-151 (2000)). It has been reported that some organic acid anions, with oxygen in hydroxyl and carboxyl groups, have the ability to form stable complexes with cations such as $Ca^{2+}$, $Fe^{2+}$, $Fe^{3+}$, and $Al^{3+}$, which are often bound to phosphate (Arcand M M, Schneider K D. Plant- and microbial-based mechanisms to improve the agronomic effectiveness of phosphate rock: a review. An Acad Bras Ciênc 78: 791-807 (2006)).

In addition, some PSMs can contribute to plant health by producing active substances against some specific pathogen plants (Vassilev N, Vassileva M, Nikolaeva I. Simultaneous P-solubilizing and biocontrol activity of microorganisms: potentials and future trends. Appl Microbiol Biotechnol 71: 137-144 (2006); Wani P A, Khan M S, Zaidi A. Chromium reduction, plant growth-promoting potentials and metal solubilization by *Bacillus* sp. isolated from alluvial soil. Curr Microbiol 54: 237-243 (2007)), which could reduce the excessive use of the chemical pesticides that constitute a threat for human health (Te-Hsiu M. The international program on plant bioassays and the report of the follow-up study after the hands-on workshop in China. Mutation Research/Fundamental and Molecular Mechanisms of Mutagenesis 426: 103-106 (1999)). Among these PSMs, Actinomycetes are of special interest. On one hand, these filamentous and sporulating bacteria are valuable decomposers of organic matter in soil communities and on the other hand, they are natural producers of antibiotics or anti-fungi that could protect the plants against various devastating phytopathogen agents (Ikeda T. Pharmacological effects of ivermectin, an antiparasitic agent for intestinal strongyloidiasis: its mode of action and clinical efficacy. Nippon Yakurigaku Zasshi 122: 527-538 (2003); Jain P K, Jain P C. Isolation, characterization and antifungal activity of *Streptomyces sampsonii* G S 1322. Indian J Exp Biol 45: 203-206 (2007)). *Streptomyces griseus*-related strains were previously selected as the most efficient RP solubilizing Actinomycetes. Such strain were isolated from Moroccan phosphate mines (Hamdali H, Bouizgarne B, Hafidi M, Lebrihi A, Virolle M J, Ouhdouch Y. Screening for rock phosphate solubilizing Actinomycetes from Moroccan phosphate mines. Appl Soil Ecol 38: 12-19 (2008)) and as a potential producer of antifungal metabolites (Hamdali H, Hafidi M, Virolle M J, Ouhdouch Y. Rock phosphate solubilizing Actinomycetes: Screening for plant growth promoting activities. World J Microbiol Biotechnol 24: 2565-2575 (2008); Hamdali H, Hafidi M, Virolle M J, Ouhdouch Y. Growth promotion and protection against damping-off of wheat by two rock phosphate solubilizing Actinomycetes in a P-deficient soil under greenhouse conditions. Appl Soil Ecol 40: 510-517 (2008)). The mechanism of RP solubilization involved the excretion of chelating substances (siderophores) (Hamdali H, Bouizgarne B, Hafidi M, Lebrihi A, Virolle M J, Ouhdouch Y. Screening for rock phosphate solubilizing Actinomycetes from Moroccan phosphate mines. Appl Soil Ecol 38: 12-19 (2008)).

During the time, bacteria have also colonized human being with who they have coexisted for thousand of years.

Even if they play a crucial function for their host life, they also contain species that are major pathogens associated with a great morbidity and mortality in human being.

Antibiotics have been greatly studied and used since the $XIX^{th}$ century to kill bacteria in human being but a major concern of their use is a systematic development of a bacterial resistance in the years following their use. (With the growing of public health awareness of disease transmissions and across-infection caused by the microorganisms, use of antimicrobial materials has been increased in many application areas like medical devices, drugs, health care and hygienic applications, water purification systems, hospital furniture, dental surgery equipment, textiles, food packaging and food storage (Gottenbos, B., Van der Mei, H., Klattern, f. & Busscher, H. J (2002). In vitro and in vivo antimicrobial activity of covalently coupled quaternary ammonium silane coating on silicone rubber. Biomaterails. 231417-1423

There is therefore a need for the discovery of new antibiotics compounds.

In the course of their study, the inventors discovered a new bacterial strain displaying mineral phosphate solubilization and antimicrobial activities against various pathogens without the drawback of those disclosed in the prior art.

One of the aims of the present invention is to provide compositions containing *Streptomyces* BG 76 strain or compounds secreted by said strain.

Another aim of the invention is to use said strain or secreted compounds as a drug, in particular as an antibiotic or antimicrobial agent.

Still another aim is to use said strain or secreted compounds for the prevention and/or control of damping-off of plants induced by microorganisms.

Still another aim of the invention is to use said strain or secreted compounds for the fertilization of plants.

Still another aim of the invention is to use said strain or secreted compounds for the purification of metals.

Still another aim of the invention is to use said strain or secreted compounds for the cleaning up of metal polluted grounds.

Still another aim of the invention is to provide processes for the prevention and/or control of damping-off of plants induced by microorganisms, for the fertilization of plants or for the purification of metals.

The present invention relates to a composition comprising the *Streptomyces* BG76 strain as deposited in the BCCM/LMB bacteria collection under accession number BCCM/LMG P-24617 on Jun. 27, 2008.

*Streptomyces* is the largest genus of Actinobacteria and of the family Streptomycetaceae.

Said *Streptomyces* BG76 strain has not been isolated from phosphate mines, in particular from Moroccan phosphate mines but from the digestive tract of the Moroccan terrestrial *Testudo graeca* (Tortue mauresque) habiting rock phosphate mine region and feeding on rock phosphate soil and animal bone fragments.

In the present specification, the term "strain" also refers to one of its variant or mutant.

A mutant of a strain contains at least one modification of the genotype of said strain provided that said mutant belongs to the same species of the strain.

A variant of a strain contains one or more modification of the genotype of said strain without altering the phenotype of said strain.

In an advantageous embodiment, the present invention relates to a composition constituted of the *Streptomyces* BG76 strain as deposited in the BCCM/LMB bacteria collection under accession number BCCM/LMG P-24617 on Jun. 27, 2008.

In an advantageous embodiment, the present invention relates to a composition defined above, comprising further one or more additional actinomycetes strains.

Actinobacteria or actinomycetes are a group of Gram-positive bacteria. They include some of the most common soil life, playing an important role in decomposition of organic materials, such as cellulose and chitin and thereby playing a vital part in organic matter turnover and carbon cycle.

Most actinobacteria of medical or economic significance are in subclass Actinobacteridae, order Actinomycetales, and several genus are found, the most important of them being the following:

*Actinomyces, Arthrobacter, Corynebacterium, Frankia, Micrococcus, Micromonospora, Mycobacterium, Nocardia, Propionibacterium, Streptomyces.*

In an advantageous embodiment, said additional actinomycetes strains defined above are different from *Streptomyces griseus*: BH7 and YH1, *Candidatus streptomyces philanti biovar coarctatus*: BH3, *Streptomyces* sp. B11: BH5, *Candidatus streptomyces philanti biovar basilaris*: BH1; *Streptomyces cavourensis*:BH2, *Micronospora aurantiaca*: KH2.

Said strains are defined in Hamdali H, et al. (Rock phosphate solubilizing Actinomycetes: Screening for plant growth promoting activities. World J Microbiol Biotechnol 24: 2565-2575 (2008)).

In an advantageous embodiment, the present invention relates to a composition defined above, further comprising or not one or more additional actinomycetes strains, wherein the total concentration of said *Streptomyces* BG76 strain alone or in combination with one or more additional actinomycetes strain, is from about $10^6$ cfu/ml to about $10^9$ cfu/ml, preferably from about $10^7$ cfu/ml to about $10^9$ cfu/ml, more preferably from about $10^7$ cfu/ml to about $10^8$ cfu/ml, in particular $10^7$ cfu/ml.

In this embodiment, the composition comprises:

either only said *Streptomyces* BG76 strain at a concentration from about $10^6$ cfu/ml to about $10^9$ cfu/ml, preferably from about $10^7$ cfu/ml to about $10^9$ cfu/ml, more preferably from about $10^7$ cfu/ml to about $10^8$ cfu/ml, in particular $10^7$ cfu/ml, or said *Streptomyces* BG76 strain in combination with one or more additional actinomycetes strain. In this last case, the total concentration of the strains is $10^6$ cfu/ml to about $10^9$ cfu/ml, preferably from about $10^7$ cfu/ml to about $10^9$ cfu/ml, more preferably from about $10^7$ cfu/ml to about $10^8$ cfu/ml, in particular $10^7$ cfu/ml.

Below $10^6$ cfu/ml, the strain concentration is too low to observe an activity.

The maximal observed effect does not change above $10^9$ cfu/ml.

In an advantageous embodiment, the present invention relates to a composition defined above, wherein said composition comprises or is constituted of the culture supernatant isolated from a culture medium of said actinomycetes strain.

By "culture medium" or "growth medium" which are equivalent term in the present application is meant a liquid or gel or solid designed to support the growth of microorganisms or cells.

The "culture medium" may be commercially available. The most common growth media for microorganisms are nutrient broths (liquid nutrient medium) or Luria Bertani medium (LB medium or Lysogeny Broth). Liquid media are often mixed with agar and poured into Petri dishes to solidify.

They may be also specifically designed for a particular micro organism.

By "culture supernatant isolated from a culture medium" is meant the liquid fraction surmounting the micro organism after growing in the culture medium and that has been removed from the culture medium.

Thus, in the present invention, the composition comprises or consists in:

either the *Streptomyces* BG76 strain further comprising or not one or more additional actinomycetes strains, or in the supernatant of the culture medium of said *Streptomyces* BG76 strain further comprising or not one or more additional actinomycetes strains.

In an advantageous embodiment, the present invention relates to a composition defined above, wherein said culture supernatant comprises or is constituted of one or more chemical compound(s) belonging to the following general formula $(A)_n M_m$, wherein:

A is a compound having the general formula (I):

wherein R1 to R3 are independently from each other:
H, a $C_1$-$C_{10}$ linear or branched alkyl group, or a $C_3$-$C_{10}$ cycloalkyl group, a halogen group, or OH, SH, $NH_2$, $NO_2$, CN, COOH, COOR in which R is a $C_1$-$C_{10}$ linear or branched alkyl group, or a $C_3$-$C_{10}$ cycloalkyl group, Z represents H, a linear or branched alkyl, a cycloalkyl, a benzyl, a linear or branched alkyl carbonyl, a cycloalkyl or a benzyl, M is a metal being in an oxidation state equal to II or III, in particular selected from the group consisting of Fe, Cu, Ni, Co, Ca, n is an integer equal to 1, 2 or 3, m is an integer equal to 0 or 1, provided that when m=0, n=1.

When m represents 0, it means that n=1 and that no metal is chelated to the compound A.

By linear alkyl group from $C_1$ to $C_{10}$ is meant a group such as methyl, ethyl, propyl, butyl, pentyl, hexyl, heptyl, octyl, nonyl, decyl.

By branched alkyl group $C_1$ to $C_{10}$ is meant an alkyl group as defined above bearing substituents selected from the list of linear alkyl groups defined above, said linear alkyl group being also liable to be branched.

Both linear and branched alkyl definitions applies to the entire specification.

By cycloalkyl group from $C_3$ to $C_{10}$ is meant a group such as cyclopropyl, cyclobutyl, cyclopentyl, cyclohexyl, cycloheptyl, cyclooctyl, cyclononyl or cyclodecyl. Such groups can also be substituted by a linear or branched alkyl group as defined above or by any other group.

The definition of cycloalkyl group applies also to the entire specification.

The compound A bears a oxime function that can be optionally under the form of oxime ether or ester, wherein the ether or ester is a linear or branched alkyl or a cycloalkyl as defined above.

A metal being in an oxidation state equal to II or III can be, without being limited to: Fe, Zn, Ni, Mn, Ru, Rh, Pb, Mo, Cd, Ca, Mg, Co, As or Cu, but advantageously the metal is selected from the group consisting of Fe, Cu, Ni, Co, Ca.

According to the invention, the general formula $(A)_n M_m$ can thus represent:
a monomer chelated or not with a metal M defined above,
a dimer or a trimer of the compound A chelated with a metal M defined above.

The chelation occurs between the oxygen atom of the oxime function in C2, the oxygen atom of the carbonyl function located in C1 and the metal of an oxidation state equal to II or III depending on the monomer, dimmer or trimer.

The chemical compounds above defined of this embodiment can be extracted and purified by methods known from a man skilled in the art, from the supernatant of the micro organism culture medium.

The compound A of general formula I can also be chemically synthesized by conventional well known method for a man skilled in the art and thus the composition of the invention relates also to a composition comprising of being constituted of a general formula $(A)_n M_m$ wherein A has been chemically synthesized and wherein the chelation has been chemically obtained.

In an advantageous embodiment, the present invention relates to a composition defined above, wherein said chemical compound is the following:

Said compound is also called Viridomycin G.

In an advantageous embodiment, the present invention relates to a composition defined above, wherein said general formula $(A)_n M_m$ or chemical compound A is grafted on a solid support to chelate or exchange metals.

The compound of general formula $(A)_n M_m$ can be linked by conventional method well known for a man skilled in the art to a solid support such as a polymer, for example a polyethylene oxide or a polyethylene glycol, by means of the aldehyde function of carbon C4 or by one of the R1 to R3 substituents.

By the expression "to chelate or exchange metals" is meant for example a purification process of an ore, in particular to separate (a) metal(s) from other components, such as uranium from phosphorites, or for removing (a) metal(s) from the soils polluted by said metal(s), such as mine soil.

Said metals must have an oxidation state equal to II or III.

The compound of general formula $(A)_n M_m$ can be previously chelated as in compound 1 and therefore an exchange of metals occurs, or the compound of general formula $(A)_n M_m$ is not previously chelated with a metal such as compound A and therefore, the metal(s) present in the ore or in the polluted soil will be chelated.

According to another aspect, the present invention relates to a compound having a general formula $(A)_n M_m$ for its use as a drug.

In an advantageous embodiment, the present invention relates to a compound having a general formula $(A)_n M_m$ for its use as a drug, wherein said drug presents an antimicrobial activity.

By the expression "antimicrobial activity" is meant a bacteriostatic and/or bactericide activity against gram+ and/or gram− bacteria.

In an advantageous, the present invention relates to method for treating a bacterial infection by administration of therapeutical amount of a compound of general formula $(A)_n M_m$ to a patient in need thereof.

In an advantageous embodiment, the present invention relates to a compound of general formula $(A)_n M_m$ for its use as a drug having an antimicrobial activity, wherein said antimicrobial activity is against Gram+bacteria, in particular bacteria selected from the group consisting of *Micrococcus luteus, Bacillus subtillis,* and *Staphylococcus aureus.*

In an advantageous embodiment, the present invention relates to a compound of general formula $(A)_n M_m$ for its use as a drug having an antimicrobial activity defined above, wherein said drug is the compound 1 defined above.

In an advantageous embodiment, the present invention relates to a compound of general formula $(A)_n M_m$, in particular to the compound 1, for its use as a drug, wherein said drug is grafted on a medical surface suitable especially for inhibiting the biofilm formation of bacteria.

Such an inhibition is suitable for chelating or exchange ions necessary to the bacteria growth and thus can give functionalized surfaces in order to obtain medical surfaces having said drug grafted with antibacterial properties.

The medical surface can be an antimicrobial material with plastic or cellulose, in particular antibacterial plastics, antibacterial fibers and antibacterial ceramics (LaCoste, A., Schaich K., & Yam, K. L. (2005) Advencing controlled release packaging trough smart blending. Packaging Technology Science, 18, 77-87)

In an advantageous embodiment, the present invention relates to a compound of general formula $(A)_n M_m$, in particular the compound 1, for its use as a drug, wherein said drug is suitable for treating diseases wherein an excess of iron and an oxidative stress is implicated, in particular hematochromatose, Parkinson disease, Alzheimer disease . . . .

In an advantageous embodiment, the present invention relates to a method for treating diseases wherein an excess of iron and an oxidative stress is implicated, in particular hematochromatose, Parkinson disease, Alzheimer disease . . . by administering a compound of general formula $(A)_n M_m$, in particular the compound 1 to a patient in need thereof.

In another aspect, the present invention relates to the use of a composition defined above, for the prevention and/or control of damping-off of plants induced by microorganisms.

The term "control" means to limit, to protect or regulate a plant against a pathogen.

By "damping-off of plants induced by microorganisms" is meant a disease caused by different micro organisms or germ, i.e. by an organism that is microscopic (usually too small to be seen by the naked human eye) in particular fungus which can kill seeds or seedlings before or after they germinate.

The term "plant" means living organisms belonging to the kingdom Plantae. They include familiar organisms such as trees, herbs, bushes, grasses, vines, ferns, mosses, and green algae.

Microorganisms are very diverse. They include bacteria, fungi, archaea, and protists; microscopic plants (called green algae); and animals such as plankton, the planarian and the amoeba.

Thus, the compositions of the invention are liable to have a bacteriostatic and/or bactericide activity against gram+ and/or gram−bacteria in plants and/or a fungistatic and/or fungicide activity on fungi in seeds and/or plants, in particular as examples only against *Fusarium oxysporum* f. sp. *albedinis, Mucor ramannianus, Pythium ultimum,* or yeast, in particular as examples only against *Candidas albicans, Rhodotorula rubra.*

In another embodiment, the present invention relates to the use of a composition comprising the *Streptomyces* BG76 strain or the supernatant of said strain, said composition having stimulation properties of plant natural defences and/or fungistatic properties, for the prevention and/or the control of micro organism induced plant diseases, In this embodiment, the composition is liable to produce indole acetic acid (IAA), known to stimulate the plant growth, and to produce enzymes such as chitinases liable to degrade chitine constituting the fungi envelop to give oligochitosanes that stimulate the natural defences of the plants against pathogen fungi.

In this embodiment, the composition is used to promote plant growth and to prevent and/or control microorganisms liable to develop on a plant once the germination has been carried out.

In another aspect, the present invention relates to the use of a composition defined above, for the solubilization of mineral phosphate.

The composition of the invention is liable to solubilize mineral phosphate such as rock phosphate (natural phosphate) or podzolane.

The solubilization process implicates the destruction by the composition, of the strong ionic bonds existing between a metal such as calcium or iron and the phosphorus present in the mineral phosphate.

The liability of solubilizing mineral phosphate allows to the compositions of the invention to promote the growth of plants by giving to the plant or to the micro-organisms of the plant soil the necessary phosphorus.

In another embodiment, the present invention relates to the use of a composition defined above, said composition having stimulation properties of plant natural defences and/or fungistatic properties and solubilization properties of mineral phosphate for the prevention and/or the control of micro organism induced plant diseases and the stimulation of plant growth.

In another aspect, the present invention relates to the use of a composition comprising a compound of general formula $(A)_n M_m$, in particular a compound of formula I, for the purification of an ore, in particular to separate a metal from other components, such as uranium from phosphorites.

The purification is obtained by destruction of ionic bonds between the components of the ore by chelating or exchange of the metal.

In another aspect, the present invention relates to the use of a composition comprising a compound of general formula $(A)_n M_m$, in particular a compound of formula I, for removing a metal(s) from the soils polluted by said metal(s), such as mine soil.

Said metals must have an oxidation state equal to II or III.

In another aspect, the present invention relates to actinomycete strain *Streptomyces* BG76 as deposited in the BCCM/LMB bacteria collection under accession number BCCM/LMG P-24617 on Jun. 27, 2008.

In an advantageous embodiment, the partial sequence of 16SrRNa of the *Streptomyces* BG76 is set fourth by SEQ ID NO:1.

In another aspect, the present invention relates to a process:
for the prevention and/or control of damping-off of plants induced by microorganisms such as *Pythium* sp., in particular *Pythium ultimum*, and/or
for the prevention and/or the control of micro organisms inducing plant diseases, and/or
for the plant growth promoting, and/or
for the solubilization of mineral phosphate, comprising a spraying step of the aerial parts and/or an inoculation step of the underground parts of said plants with a composition such as defined in above.

In an advantageous embodiment, said composition comprises *Streptomyces* BG76 strain alone or in combination with one or more additional actinomycetes strain, in a total concentration from about $10^6$ cfu/ml to about $10^9$ cfu/ml, preferably from about $10^7$ cfu/ml to about $10^9$ cfu/ml, more preferably from about $10^7$ cfu/ml to about $10^8$ cfu/ml, in particular $10^7$ cfu/ml.

In an advantageous embodiment, the present invention relates to a process defined above, wherein said spraying step of the aerial parts and/or an inoculation step of the underground parts of said plants is carried out with one or more chemical compound(s) belonging to the general formula $(A)_n M_m$ such as defined above.

In an advantageous embodiment, said compound of formula $(A)_n M_m$ is preferably at a concentration in the composition from about $10^{-3}$ M to about $10^{-9}$ M, preferably from about $10^{-4}$ M to about $10^{-9}$ M, more preferably from about $10^{-5}$ M to about $10^{-9}$ M, more preferably from about $10^{-6}$ M to about $10^{-9}$ M, more preferably from about $10^{-7}$ M to about $10^{-9}$ M, more preferably from about $10^{-8}$ M to about $10^{-9}$ M, more preferably from about $10^{-7}$ M to about $10^{-8}$ M, and more preferably from about $10^{-6}$ M to about $10^{-7}$ M.).

In an advantageous embodiment, the present invention relates to a process for the plant growth promoting defined above, comprising further the administration of mineral phosphate.

In an advantageous embodiment, the present invention relates to a process for the purification of an ore, in particular to separate a metal from other components, comprising contacting an ore with a composition defined above.

In an advantageous embodiment, the metal of the ore is uranium.

DESCRIPTION OF THE FIGURES

FIG. 1A presents the *Streptomyces* BG76 strain during its producing phase of the green pigment (circles) responsive for the solubilization and the bio control.

Figure B presents the *Streptomyces* BG76 strain during its exponential growing phase without visualizing the green pigment excretion.

FIG. 2A: magnification 3,000

FIG. 2B: magnification 15,000

The arcs represent the HMBC correlation (H→C)

x-axis: Viridomycin G compound (compound 1) (μL)

y-axis: P solubilized μg/mL

Black histogram: RP: rock phosphate

White histogram: TC: tricalcium phosphate

EXAMPLES

Example 1

Isolation of *Streptomyces* sp. BG76

The Actinomycete strain *Streptomyces* sp. BG76 was isolated from the digestive tracts (gut) of the Moroccan terrestrial *Testudo graeca* (Tortue mauresque) habiting rock phosphate mine region and feeding on rock phosphate soil and small animal bone fragments. The isolation method was used according to the following strategy:

a) Sampling

The digestive tracts excretions of the Moroccan terrestrial (Tortue mauresque) *Testudo graeca* was sterilely collected.

The samples from each replicate area were then homogenized and placed in a sterile tightly closed polyethylene bag. The samples were stored at 48° C. and processed within 48 h.

b) Sample Treatment and Culture Conditions

Two gram (wet weight) of each sample were suspended in 18 ml of sterile physiological serum (9 g·l$^{-1}$, NaCl), homogenized, shaken on a rotatory shaker (200 rev min$^{-1}$ (2 g)) for 30 min. Then, 0.1 ml of various dilutions of the treated samples was plated in triplicate on the surface of several known Actinomycetes isolation media (see list in point c)) and of a solid medium prepared with RP soil extracts (RPSEA see d)) with glycerol (5 g l$^{-1}$) and agar (15 g l$^{-1}$) being added to these extracts. The pH was adjusted to 7 and the medium was sterilized at 121° C. for 20 min. These media were supplemented with 40 µg ml$^{-1}$ actidione and 10 µg ml$^{-1}$ nalidixic acid, growth inhibitors of fungi and Gram negative bacteria, respectively. After plating, the agar plates were incubated for 21 days at 28° C. in order to allow growth of the slow growing Actinomycetes. Actinomycetes were recognized on the basis of morphological and physiologically features following the International *Streptomyces* Project (ISP) (Shirling and Gottlieb, 1966). Morphological characteristics were studied under light microscope after growing the culture on oatmeal agar.

c) List of Actinomycete Isolation Known Media

Triplicate plates of the following media: Olson's (O) (Olson 1968), Lindenbein modified by Benedict (LB) (Porter et al. 1960), Nakeeb and Lechevalier (NL) (Nakeeb and Lechevalier 1963), Kuster and williams (KW) (Kuster and Williams 1964), Lingappa and Lockwood (LL) (Lingappa and Lockwood 1962), M3 medium (Rowbotham and Cross 1977) were used for actinomycete isolation. These media were supplemented with cyloheximide (40 µg ml$^{-1}$) which found to inhibit the growth of fungi.

d) Rock Phosphate Soil Extract Preparation (RPSEA) and Selection of Rare Isolates Equal volume of the rock phosphate soil (terrestrial Tortue mauresque habitat) of investigated Moroccan rock phosphate soil region and distilled water were macerated overnight and sterilized by filtration. Agar was added to the collected filtrate and the pH was adjusted to 7.0 before sterilization. To increase the selectivity of this medium glycerol (0.5%) and nalidixic acid (10 mg·l$^{-1}$) were added.

*Streptomyces* sp. BG76 and other isolates that were able to grow well on RPSEA but not on the majority of well known actinomycetes isolation tested media were considered as rare. The capability to use rock and tricalcium phosphate as unique source of phosphate was the main selection criteria.

Examples 2

Taxonomic Characterisation of Strain *Streptomyces* sp. BG76

The taxonomic status of strain *Streptomyces* sp. BG76 was established using a polyphasic approach. The organism was found to have morphological and chemotaxonomic characteristics typical of Streptomycetes.

a) Morphological Properties:

On solid media the strain *Streptomyces* sp. BG76 gave thin powdery and irregular colonies. Under light microscopy, substrate mycelia are not fragmented and the aerial hyphae are bearing rectiflexible spore chains. Spores are of cylindrical shape of about 0.75 to 0.95 µm long and about 0.55 to 0.6 µm in diameter with smooth surfaces (FIGS. 1A, 1B and 2A, 2B). No synnemata, sclerotia or sporangia were observed.

b) Properties in Various Media:

The exemplary strain of the invention shows the following properties when incubated at 28° C. in the following various solid media:

On Yeast Extract-Malt Extract Agar (ISP2), abundant white-grey growth; green substrate mycelium, soluble green pigment.

On Oatmeal Agar (ISP3), abundant grey growth for substrate mycelium and green one for aerial mycelium, no soluble pigment.

On Inorganic Salt Starch Agar (ISP4), abundant green aerial growth, mauve substrate mycelium, no soluble pigment.

On Glycerol-Asparagine Agar (ISP5), abundant brown growth, orange-brownish substrate mycelium, no soluble pigment.

On Pepton Yeast Extract Iron Agar (ISP6), creamy white growth, green vegetative mycelium, green soluble pigment.

On Tyrosine Agar (ISP7), abundant white-gray growth, creamy substrate mycelium, no soluble pigment.

On Sucrose Nitrate Agar, abundant white growth, white-greenwish substrate mycelium, no soluble pigment.

On Sucrose Czapeck Agar, abundant cream growth for aerial mycelium and green substrate mycelium, green soluble pigment.

On Glucose Asparagine Agar, thin creamy growth for both aerial and substrate mycelia, no soluble pigment.

On Olson's medium, abundant white growth, yellow-brownish substrate mycelium, no soluble pigment.

On Bennett's Agar, abundant white-gray aerial mycelium, green vegetative mycelium, green soluble pigment.

On Nutrient Agar, abundant cream growth for aerial mycelium and yellow substrate mycelium, yellow soluble pigment.

c) Physiological Properties:

The strain of the invention was catalase positive, oxydase positive and nitrate reductase positive. The optimal growth was obtained for a temperature between 28 to 30° C. The strain grew in nutrient agar medium containing 15 g/l of NaCl and metabolized D-glucose, fructose, sucrose, L-rhamnose, mannose, maltose, lactose, galactose, D-raffinose, arabinose, starch, glycerol, sorbitol, inositol and citrate.

The strain *Streptomyces* sp. BG76 was sensitive to novobiocin, polymexin B, cefalotin B, gentamycine and bacitracine. The strain was resistant to sulfamide.

d) Chemotaxonomy:

The cell wall of strain *Streptomyces* sp. BG76 contained LL isomer of diaminopimelic acid and the strain was assigned to cell wall chemotype I which characterised the genus of *Streptomyces*.

e) Biochemical and Morphological Characteristics of Strain *Streptomyces* sp. BG76

Characteristics are given in Table I:

TABLE I

| Characteristics | *Streptomyces* sp. BG76 |
|---|---|
| ISP3 | +++ |
| ISP4 | +++ |

TABLE I-continued

| Characteristics | Streptomyces sp. BG76 |
|---|---|
| ISP6 | + |
| Aerial spore mass | green |
| Colony reverse | cream |
| Soluble pigment | − |
| Spore morphology | RF |
| DAP-isomer | LL |
| Gram staining | + |
| Tyrosin hydrolysis | + |
| Nitrate reduction | + |
| Catalase | + |
| Oxidase | + |
| Carbone source utilization | |
| Sucrose | + |
| Fructose | + |
| Glucose | + |
| Glycerol | + |
| Maltose | + |
| Lactose | + |
| Mannose | + |
| Citrate | + |
| Mannitol | + |
| Galactose | + |
| Inositol | + |
| Rhamnose | + |
| Xylose | + |
| D-Raffinose | + |
| Sorbitol | + |
| Arabinose | + |
| Antibiotic sensibility | |
| Novobiocine (30 µg) | S |
| Polymyxin B (300 U) | S |
| Cefalotin (30 µg) | S |
| Gentamycine (10 µg) | S |
| Bacitracine (10 U) | S |
| Sulfamides (250 µg) | R |

+++: maximal growth of the BG76 strain with said medium
+: tested positive versus said activity or utilizes said carbon source as substrate;
−: tested negative versus said activity or does not utilize said carbon source as substrate.
RF: rectiflexible,
R: resistant,
S: sensitive,
LL: Absolute configuration of diaminopimelic acid.

e) Molecular Taxonomy:

The partial sequencing of 16S rRNA of strain *Streptomyces* sp. BG76 using the specific primer gives the SEQ ID NO:1 (Sequence for gamma region). The 16S rDNA was amplified using the PCR method with Taq DNA polymerase (Qiagen, USA) and universal primers PA (5'-AGAGTTTGATCCTG-GCTCAG-3') as set forth in SEQ ID NO: 2 and PH (5'-AAGGAGGTGATCCAGCCGCA-3') as set forth in SEQ ID NO: 3.

Phylogenetic analysis based on the almost complete 16S rRNA gene sequence indicated that the novel isolate belongs to the genus *Streptomyces* and consistently falls into Glade together with *Streptomyces griseus*, *Streptomyces* anulatus strain NRRL 8-2873, *Streptomyces* sp. YIM 80147. The complete 16SrDNA gene sequences of strain *Streptomyces* sp. BG76 show highest similarity of 98.6% to the type strain of *Streptomyces* anulatus strain NRRL 8-2873 and 98.7% and to a strain of *Streptomyces griseus*. However, DNA-DNA relatedness and phenotypic data distinguished the strain *Streptomyces* sp. BG76 from these phylogenetically related type strains. It is therefore concluded that strain *Streptomyces* sp. BG76 deposed in the BCCM/LMB Bacteria collection (Laboratorium voor Microbiolgie K. L. Ledeganckstraat B-9000 Gent Belgium) under accession number BCCM/LMG P-24617 on Jun. 27, 2008 represents a novel species of the genus *Streptomyces*.

On the basis of this analysis strain *Streptomyces* sp. BG76 represents strain of new species within the genus *Streptomyces*.

Examples 3

Antimicrobial Activity of *Streptomyces* sp. BG76 Strain

The following strains were used to evaluate the antimicrobial activities of the strain *Streptomyces* sp. BG76 and its produced antimicrobial compounds:

the Gram positive bacteria *Micrococcus luteus* ATCC 381, *Bacillus subtilis* ATCC 9524 and *Staphylococcus aureus* DSM 20231 (ATCC 12600), the yeast *Candidas albicans* ATCC 2091, *Rhodotorula rubra* Tü 8093, and the phytopathogenic fungi *Mucor ramannianus*, *Fusarium oxysporum* f. sp. *albedinis* and *Pythium ultimum* (strains collection of Microbiology Laboratory, Marrakech).

The antimicrobial activity was determined by the plate diffusion method (Bauer et al. 1996). Isolates were grown on agar-Bennett medium for 14 days and three discs (10 mm in diameter) were cut and placed on nutrient agar (Difco, USA) (for bacteria and yeasts) and Sabauroud medium (Biorad, France) (for fungi) which were seeded with appropriate test organism. Plates were first kept in at 4° C. for at least 2 h to allow the diffusion of produced antibiotics, then incubated at 30° C. Sizes of the inhibition zones were determined after 24 h of incubation for bacteria and yeasts and 48 h for fungi. Controls involved the use of sterile agar plugs. Three replicates were performed for each isolate by each microorganism test. The antimicrobial activities of the new strain *Streptmoyces* sp. BG76 is shown in the following table II.

TABLE II

In vitro antimicrobial activities of *Streptomyces* sp. BG76 strain

| | Microorganism tested | Diameter of inhibition zone (mm)* |
|---|---|---|
| Gram positive | *Micrococcus luteus* ATCC 381 | 26.0 ± 0.02 |
| | *Bacillus subtilis* ATCC 9524 | 18.6 ± 0.01 |
| | *Staphylococcus aureus* DSM 20231 | 22.2 ± 0.04 |
| Yeast | *Candidas albicans* ATCC 2091 | 23.6 ± 0.02 |
| | *Rhodotorula rubra* Tü 8093 | 20.1 ± 0.03 |
| Fungi | *Fusarium oxysporum* f.sp. *albedinis* | 25.2 ± 0.01 |
| | *Mucor ramannianus* | 28.5 ± 0.01 |
| | *Pythium ultimum* | 28.6 ± 0.04 |

*Values given are the means of 3 replicates

Example 4

Fermentation and Isolation of Compound 1

The fermentation carried out for the production of the exemplary antibiotic of the invention by using the strain of the invention comprises the steps of cultivating the strain *Streptomyces* sp. BG76 inoculated at $10^6$ spores $ml^{-1}$ in 3 liter cultures of liquid SE (pH 7.2) supplemented with 0.1% of tri-calcium phosphate as sole phosphate source. Cultures were grown for 5 days at 28° C. under constant agitation on a rotary shaker (180 g/minute After centrifuging the samples at 10,000×g for 10 minutes, the supernatant was filtered through a 0.45 μm-pore-size filter (Supor-450; Pall Corporation) to remove cells debris. The filtrate with a pH value above 7.5 was extracted at 100:25 (v/v) with isoamyl alcohol (3-methyl 1-butanol, Sigma) acidified to pH 2 with HCl 6N. The organic phase was collected and concentrated to dryness under vacuum on Rotavapor (Laborata 4000, Heidolph) under 40° C. and dissolved in 6 mL of MeOH to obtain the crude extract.

The crude extract (1.65 g) was then subjected for the detection of products by bioautography (Betina V., J. Chromat. 78, 41-51, 1973). 40 μL (*Bacillus subtilis* ATCC 9524) or 60 μL (*Pythium ultimum*, strain collection of Microbiology Laboratory, Marrakech) of the extract were spotted onto 20×20-cm silica gel plates (Merck Art. 5735, Kiesselgel 60F254), and then eluted by a mixture of ethyl acetate/methanol (100:15, v/v). The developed TLC plates were air-dried overnight at 37° C. to remove the solvents. The separated spots were visualized at 254 nm under UV light (absorbance) and at 365 nm (fluorescence). The TLC plates were then placed in a plastic bioassay dish (23×23×2.2 cm$^3$, Fisher Scientific Labosi) and overlaid with 150 ml of nutrient agar or PDA agar media (containing 7 g/L of agar), seeded respectively with *B. subtilis* or *P. ultimum*. When the agar had set, the plate was incubated at 30° C. The inhibition zones of the active fraction were determined after 24 h of incubation for *P. ultimum* and 48 h for *B. subtilis*. Clear areas due to micro-organism growth inhibition were detected, indicating the location of antibiotic compounds on the TLC plates. On analytic TLC plates, four active spots were detected by bioautography at 0.9, 0.45, 0.37 and 0.3 Rf values and designated by A, B, C and D, respectively. The results demonstrated that only the D fraction showed an efficient ability to solubilize RP as well as tricalcium phoasphate (TC). The concentrations of solubilized Phosphate from RP and TC, was 63.7 μg·mL$^{-1}$ and 135.2 μg·mL$^{-1}$, respectively.

Figure 4:
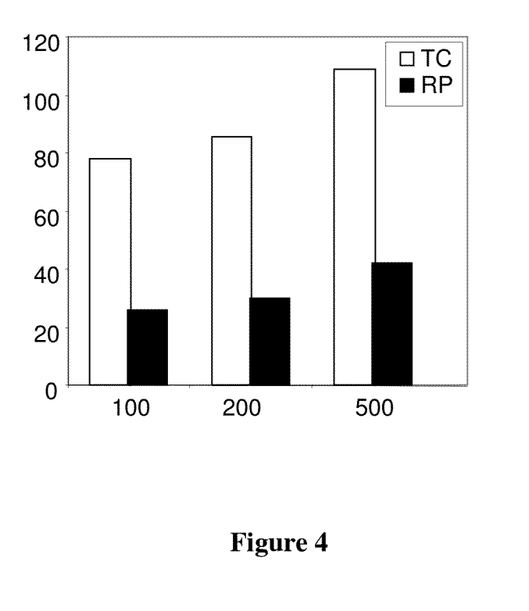
FIG. 4 represents the Mineral phosphate solubilization ability of Compound 1 according to example 6.

HPLC chromatogram of the active green fraction (D) revealed different peaks. The retention time of the main peaks $D_1$ and $D_2$ were 15.62 and 17.99 min, respectively. These fractions were checked again for both activities with mineral phosphate solubilization test and anti microbial bioassay, against ML, BS, PU and MR using the paper filter disk technique. The result showed that all strains were inhibited on the standard media by the purified $D_2$ compound indicating its strong antimicrobial (Table 1) and mineral phosphate solubilization activities (FIG. 4). D1 compound only showed an antibacterial ability.

The work up and the pathway of the isolation to get the pure compound 1 is illustrated in the scheme below:

Crude extract (1.65 g)
isoamyl alcohol acidified to pH 2 with HCl 6N Distribution
Organic phase    aqueous phase Bioautography, Silica gel column, ethyl acetate/methanol (100: 15, v/v)

8 fractions (fraction N° 5 is active against tested bacteria and fungi with mineral phosphate solubilization ability)

Preparative Thin layer chromatography (methanol/gradient, gradient 0 to 100%)

2 fractions (fraction N° 2 (D2) shows both mineral phosphate solubilization and antimicrobial activities)

Analytical Thin layer chromatography of D2 (methanol/H$_2$O 95:5)

Compound 1 (corresponding to D2, 30 mg) (a green colour compound sparingly soluble in isoamyl alcohol, ethyl acetate, methanol, H$_2$O with an Rf = 0.3 ethyl acetate/Methanol 100:15)

The bio-autography and the chemical screening were done for each step of the purification of Compound 1. The crude extracts for each step were used to do the thin layer chomatography (TLC). These were evaluated under day-light, UV-light, after staining with anisaldheyde/sulfuric acid, Ehrlish'reagent and INPTC (2-(p-Iodophenyl-)-3(p-nitrophenyl)-5-phenyl-2H-tetrazoliumchlorid).

The purity of Compound 1 was performed by analytical WATERS high performance liquid chromatography (HPLC) equipped with a RP C18 reverse phase column 7 μm (7 mm i.d×300 mm). The mobile phase used was methanol water (HPLC grade), linear gradient from 0% Methanol to 100% Water the flow rate for 1 ml/min.

Example 5

Structure Elucidation of the Antibiotic Compound 1

The structure elucidation of the exemplary antibiotic of the invention was derived from a variety of the electroscopy mass spectrum, one-dimensional and two-dimentional NMR spectra ($^1$H-NMR, $^{13}$C-NMR, COSY, HSQC, HMBC, NOESY and DOSY) as described in the following procedures:

After purification, the structure of active Compound 1 (30 mg) was elucidated by different spectroscopic methods. The results showed that the molecular formula of Compound 1 was determined as $C_{21}H_{12}O_9N_3Fe$ by HR-ESIMS and $^{13}$C NMR spectra. The ESIMS spectrum obtained in the full scan mass range (200-2000 m/z) and in the negative mode, showed two main peaks at m/z=506.0 (Calcd, 506.1875), and at m/z=1035, corresponding at (M-H)$^-$ and (2M+Na-2H)$^-$, respectively. Assignments of protons and carbons in the NMR spectra of Compound 1 are summarized in Table III.

TABLE III

NMR Assignments of Compound 1 in CD$_3$CN

| C-No. | $\delta_{C\,ppm}$ | $\delta_{H\,ppm}$ | HMBC * |
|---|---|---|---|
| 1 | 182.0 | | |
| 2 | 159.3 | | |
| 3 | 115.7 | 7.56 s | Observed |
| 4 | 123.9 | | Observed |

TABLE III-continued

NMR Assignments of Compound 1 in $CD_3CN$

| C-No. | $\delta_{C\,ppm}$ | $\delta_{H\,ppm}$ | HMBC * |
|---|---|---|---|
| 5 | 134.5 | 7.96 d (9) | Observed |
| 6 | 122.5 | 7.16 d (9) | |
| 7 | 190.5 | 9.78 s | |

Coupling constants in Hertz are given in parentheses.
* HMBC: heteronuclear multiple bond correlation Analysis of $^{13}C$ NMR spectra and $^{1}H$ NMR spectra revealed the presence of a cetone group and an aldehyde group, and three 'potential' aromatic protons, on the same moiety.

According to the green color of the chromophore moiety of this compound, to its atomic composition and to the NMR data we identified the moiety as the following monomer: the 3-imino-4-oxo-cyclohexa-1,5-diene-carbaldehydro residue.

Figure 1:
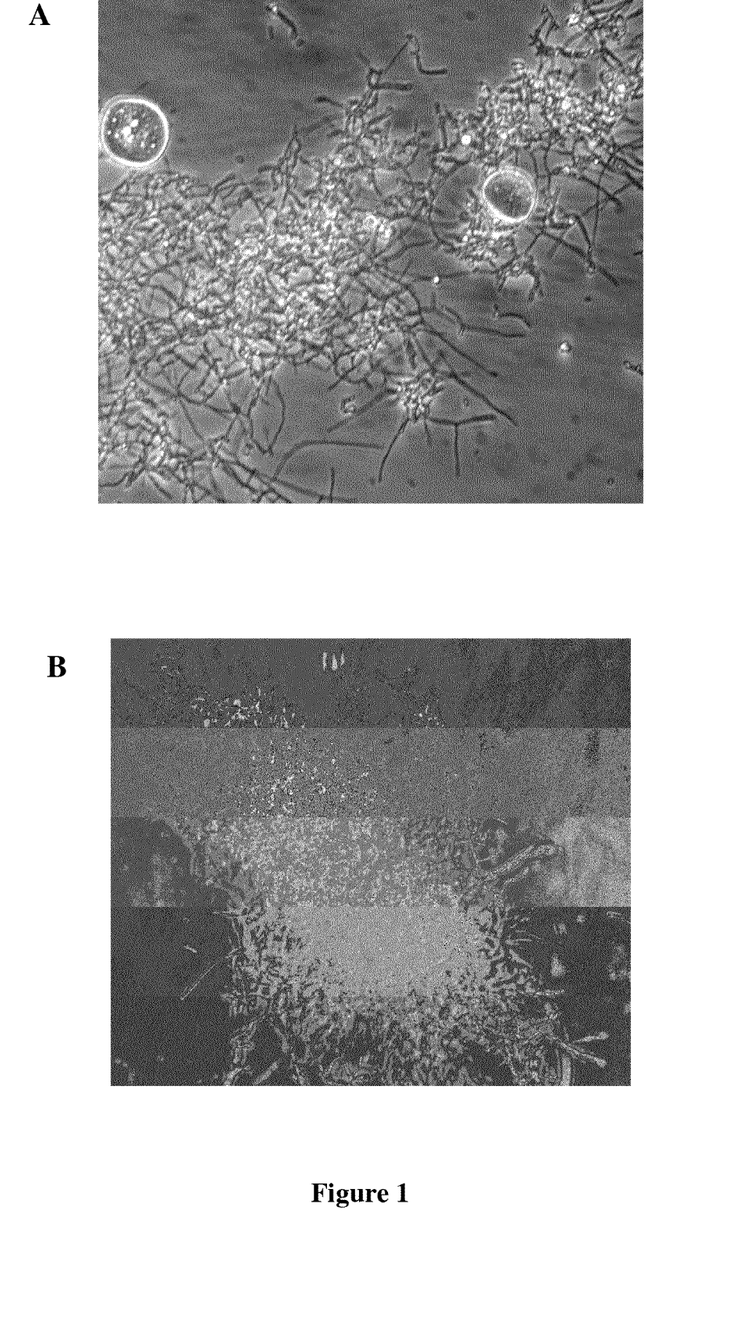
FIGS. 1A and 1B represent the light micrograph of strain *Streptomyces* BG76 after 14 days of incubation on International *Streptomyces* Project (ISP) medium N° 3 (400) (Shirling and Gottlieb, 1966).
Figure 2:
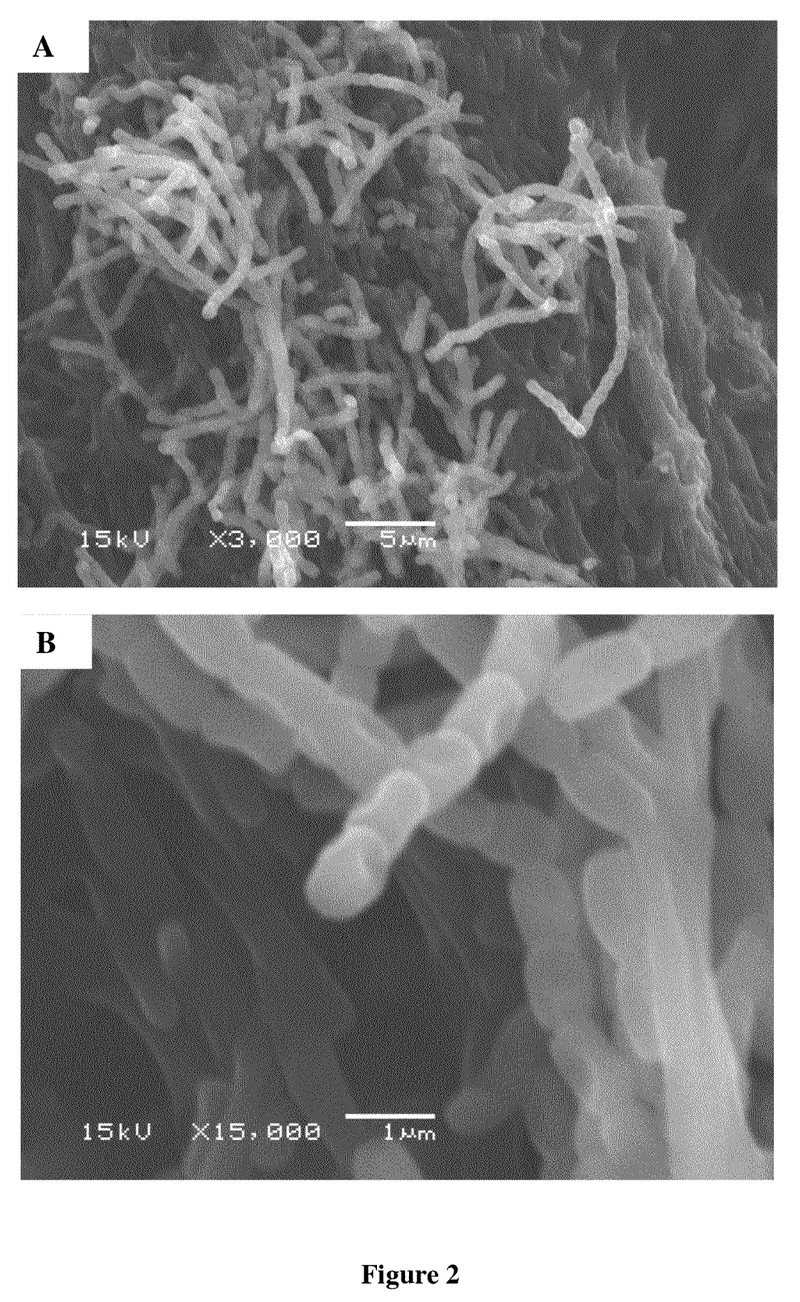
FIGS. 2A and 2B represent the scanning electron micrograph of strain *Streptomyces* sp. BG76 after 14 days of incubation on ISP medium N° 3.
Figure 3:
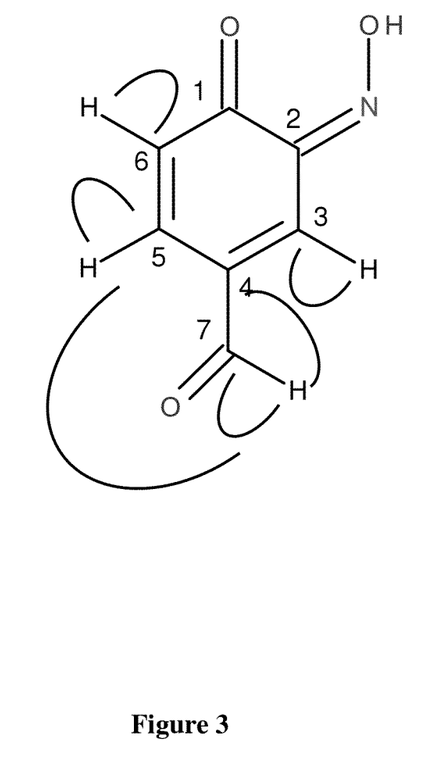
FIG. 3 represents the structure of the monomer of Compound 1 and heteronuclear multiple bond correlation (HMBC).

This monomer, shown in FIG. 3 is a monomer of the Compound 1.

The δ values and coupling patterns of four protons on the cyclohexa ring of the chromophore (Table III) and the long-range couplings between the aldehyde proton and the ring carbons indicated that the aldehyde group is present at C-7 of the monomer (FIG. 3). These results showed that the monomer should have a ketone group at C-1 and an oxim group (—C=N—O) at C-2 of the partial structure to fulfill molecular formula of Compound 1.

According to the mass spectrometry and to the various NMR measurements (COSY, HSQC, HMBC, NOESY, DOSY), the structure of Compound 1 was identified as Tris (3-imino-4-oxo-cyclohexa-1,5-diene-carbaldehydro) iron (III). The presence of iron in Compound 1 is confirmed with the atomic absorption spectrophotometer method.

Conclusion:

The antibiotic of the invention is a green compound soluble in methanol and water, and it has a molecular formula $C_{21}H_{12}O_9N_3Fe$.

Example 6

Test for the Mineral Phosphate Solubilization of Compound 1 of the Invention

The purified Compound 1 active (at final concentration 98.5 mg·mL$^{-1}$) was checked for it ability to solubilize rock phoasphate (RP) and tricalcium phosphate (TC). The results demonstrated that the Compound 1 showed an efficient ability to solubilize RP as well as TC. The concentrations of solubilized Phosphate from RP and TC, were 63.7 μg·mL$^{-1}$ and 135.2 μg·mL$^{-1}$, respectively (FIG. 4).

Example 7

Test for the Antimicrobial of the Invention "Compound 1"

The purified Viridomycin (compound 1) was checked for anti microbial bioassay, against *Micrococcus luteus* ATCC 381 (ML), *Bacillus subtilis* ATCC 9524 (BS) and the phytopathogenic fungi *Pythium ultimum* (PU) and *Mucor ramannianus* NRRL 1829 (MR) using the paper filter disk technique. The result showed that all strains were inhibited on the standard media by the purified Compound 1 indicating its strong antimicrobial activity (Table IV).

TABLE IV

Antimicrobial activity of Compound 1

| | Antimicrobial activity[a] against | | | |
|---|---|---|---|---|
| | Gram positive bacteria | | Fungi | |
| | *Bacillus subtilis* | *Micrococcus luteus* | *Pythium ultimum* | *Mucor ramannianus* |
| Diameter of microbial growth inhibition zone | 29 mm | 45 mm | 27 mm | 38 mm |

[a]Activity assessed by the agar diffusion method (filter disc i.d. 6 mm, c = 20 μg/mL, 20 μL/disc).

---

The invention claimed is:

1. A process for prevention and/or control of damping-off of plants induced by microorganisms, comprising spraying aerial parts and/or inoculating underground parts of said plants with one or more compound(s) belonging to the general formula $(A)_n M_m$, wherein:

A is a compound having the formula (I):

(I)

R1, R2 and R3 are each independently H, a $C_1$-$C_{10}$ linear or branched alkyl group, a $C_3$-$C_{10}$ cycloalkyl group, a halogen group, OH, SH, $NH_2$, $NO_2$, CN, COOH, or COOR in which R is a $C_1$-$C_{10}$ linear or branched alkyl group or a $C_3$-$C_{10}$ cycloalkyl group;

Z represents H, an alkyl or benzyl ether, or an alkyl or benzyl ester;

M is a metal being in an oxidation state equal to II or III;

n is an integer equal to 1, 2 or 3; and m is an integer equal to 0 or 1, provided that when m=0 then n=1.

2. The process of claim 1, wherein said microorganism is *Pythium* sp.

3. The process of claim 1, wherein said microorganism is *Pythium ultimum*.

4. The process of claim 1, wherein M is a metal selected from the group consisting of Fe, Cu, Ni, Co, and Ca.

5. The process of claim 1, wherein the one or more compound belonging to the general formula $(A)_n M_m$ is 6. A process for controlling microorganisms that induce diseases in plants, comprising spraying aerial parts and/or inoculating underground parts of said plants with one or more compound(s) belonging to the general formula $(A)_n M_m$, wherein:

A is a compound having the formula (I):

(I)

R1, R2 and R3 are each independently H, a $C_1$-$C_{10}$ linear or branched alkyl group, a $C_3$-$C_{10}$ cycloalkyl group, a halogen group, OH, SH, $NH_2$, $NO_2$, CN, COOH, or COOR in which R is a $C_1$-$C_{10}$ linear or branched alkyl group or a $C_3$-$C_{10}$ cycloalkyl group;

Z represents H, an alkyl or benzyl ether, or an alkyl or benzyl ester;

M is a metal being in an oxidation state equal to II or III;

n is an integer equal to 1, 2 or 3; and m is an integer equal to 0 or 1, provided that when m=0 then n=1.

7. The process of claim 6, wherein said microorganism is *Pythium* sp.

8. The process of claim 6, wherein said microorganism is *Pythium ultimum*.

9. The process of claim 6, wherein M is a metal selected from the group consisting of Fe, Cu, Ni, Co, and Ca.

10. The process of claim 6, wherein the one or more compound belonging to the general formula $(A)_n M_m$ is 11. A process for promoting growth of plants, comprising spraying aerial parts and/or inoculating underground parts of said plants with one or more compound(s) belonging to the general formula $(A)_n M_m$, wherein:

A is a compound having the formula (I):

R1, R2 and R3 are each independently H, a $C_1$-$C_{10}$ linear or branched alkyl group, a $C_3$-$C_{10}$ cycloalkyl group, a halogen group, OH, SH, $NH_2$, $NO_2$, CN, COOH, or COOR in which R is a $C_1$-$C_{10}$ linear or branched alkyl group or a $C_3$-$C_{10}$ cycloalkyl group;

Z represents H, an alkyl or benzyl ether, or an alkyl or benzyl ester;

M is a metal being in an oxidation state equal to II or III;

n is an integer equal to 1, 2 or 3; and m is an integer equal to 0 or 1, provided that when m=0 then n=1.

12. The process of claim 11, wherein M is a metal selected from the group consisting of Fe, Cu, Ni, Co, and Ca.

13. The process of claim 11, wherein the one or more compound belonging to the general formula $(A)_n M_m$ is 14. The process of claim 11, further comprising the administration of mineral phosphate to said plant.

15. A process for solubilizing mineral phosphate, comprising inoculating underground parts of plants with one or more compound(s) belonging to the general formula $(A)_n M_m$, wherein:

A is a compound having the formula (I):

R1, R2 and R3 are each independently H, a $C_1$-$C_{10}$ linear or branched alkyl group, a $C_3$-$C_{10}$ cycloalkyl group, a halogen group, OH, SH, $NH_2$, $NO_2$, CN, COOH, or COOR in which R is a $C_1$-$C_{10}$ linear or branched alkyl group or a $C_3$-$C_{10}$ cycloalkyl group;

Z represents H, an alkyl or benzyl ether, or an alkyl or benzyl ester;

M is a metal being in an oxidation state equal to II or III;

n is an integer equal to 1, 2 or 3; and m is an integer equal to 0 or 1, provided that when m=0 then n=1.

16. The process of claim 15, wherein M is a metal selected from the group consisting of Fe, Cu, Ni, Co, and Ca.

17. The process of claim 15, wherein the one or more compound belonging to the general formula $(A)_n M_m$ is

* * * * *

SEQUENCE LISTING

```
<160> NUMBER OF SEQ ID NOS: 3

<210> SEQ ID NO 1
<211> LENGTH: 1432
<212> TYPE: DNA
<213> ORGANISM: Artificial Sequence
<220> FEATURE:
<223> OTHER INFORMATION: Streptomyces sp. BG76   16S rRNA
<220> FEATURE:
<221> NAME/KEY: misc_feature
<222> LOCATION: (1)..(1432)
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (273)..(273)
<223> OTHER INFORMATION: n is a, c, g, or t
```

<220> FEATURE:
<221> NAME/KEY: misc_feature
<222> LOCATION: (1225)..(1225)
<223> OTHER INFORMATION: n is a, c, g, or t
<220> FEATURE:
<221> NAME/KEY: misc_feature
<222> LOCATION: (1416)..(1416)
<223> OTHER INFORMATION: n is a, c, g, or t

<400> SEQUENCE: 1

```
ctagatctca ngattaagcc tttcggggtg gattantggc gaacgggtga gtaacacgtg      60
ggcaatctgc ccttcactct gggacaagcc ctggaaacag ggtctaatac cggataacac     120
tctgtcccgc atgggacggg gttaaaagct ccggcggtga aggatgagcc cgcggcctat     180
cagcttgttg gtggggtaat ggcctaccaa ggcgacgacg ggtagccggc ctgagagggc     240
gaccggccac actgggactg agacacggcc canactccta cggaggcag cagtggggaa      300
tattgcacaa tgggcgaaag cctgatgcag cgacgccgcg tgagggatga cggccttcgg     360
gttgtaaacc tctttcagca gggaagaagc gaaagtgacg gtacctgcag aagaagcgcc     420
ggctaactac gtgccagcag ccgcggtaat acgtagggcg caagcgttgt ccggaattat     480
tgggcgtaaa gagctcgtag gcggcttgtc acgtcggatg tgaaagcccg ggcttaacc      540
ccgggtctgc attcgatacg ggctagctag agtgtggtag gggagatcgg aattcctggt     600
gtagcggtga aatgcgcaga tatcaggagg aacaccggtg gcgaaggcgg atctctgggc     660
cattactgac gctgaggagc gaaagcgtgg gggagcgaac aggattagat accctgggta     720
gtccacgccg taaacgttgg gaactaggtg ttggcgacat tccacgttcg tcggtgccgc     780
agctaacgca ttaaatttcc ccgcctgggg gagtacggcc gcaaggctaa aactcaaagg     840
aattgacggg ggcccgcaca agcagcggag catgtggctt aattcgacgc aacgcgaaga     900
accttaccaa ggcttgacat ataccggaaa gcatcagaga tggtgcccc cttgtggtcg      960
gtatacaggt ggtgcatggc tgtcgtcagc tcgtgtcgtg agatgttggg ttaagtcccg    1020
caacgagcgc aaccccttgtt ctgtgttgcc agcatgccct cgggtgat ggggactcac    1080
aggagactgc cggggtcaac tcggaggaag gtggggacga cgtcaagtca tcatgccct     1140
tatgtcttgg gctgcacacg tgctacaatg gccggtacaa tgagctgcga tgccgcgagg    1200
cggagcgaat ctcaaaaagc cggtntcagt tcggattggg gtctgcaact cgaccccatg    1260
aagtcggagt tgctagtaat cgcagatcag cattgctgcg gtgaatacgt tcccgggcct    1320
tgtacacacc gcccgtcacg tcacgaaagt cggtaacacc cgaagccggt ggcccaaccc    1380
cttgtgggag ggagctgtcg aaggtgggat cttatnaagt ttgatccaag tt            1432
```

<210> SEQ ID NO 2
<211> LENGTH: 20
<212> TYPE: DNA
<213> ORGANISM: Artificial sequence
<220> FEATURE:
<223> OTHER INFORMATION: Primer PA
<220> FEATURE:
<221> NAME/KEY: misc_feature
<222> LOCATION: (1)..(20)

```
<400> SEQUENCE: 2
agagtttgat cctggctcag                                              20

<210> SEQ ID NO 3
<211> LENGTH: 20
<212> TYPE: DNA
<213> ORGANISM: Artificial sequence
<220> FEATURE:
<223> OTHER INFORMATION: Primer PH
<220> FEATURE:
<221> NAME/KEY: misc_feature
<222> LOCATION: (1)..(20)

<400> SEQUENCE: 3
aaggaggtga tccagccgca                                              20
```